United States Patent
Limbach et al.

(10) Patent No.: US 9,296,678 B2
(45) Date of Patent: Mar. 29, 2016

(54) INJECTABLE FORMULATION FOR TREATMENT AND PROTECTION OF PATIENTS HAVING AN INFLAMMATORY REACTION OR AN ISCHEMIA-REPERFUSION EVENT

(71) Applicants: UNIVERSITY OF ZURICH, Zurich (CH); ETH ZURICH, Zurich (CH)

(72) Inventors: Ludwig K. Limbach, Zurich (CH); Inge K. Herrmann, Zurich (CH); Beatrice Beck-Schimmer, Zumikon (CH); Wendelin J. Stark, Zurich (CH); Martin Urner, Zurich (CH)

(73) Assignees: UNIVERSITY OF ZURICH, Zurich (CH); ETH ZURICH, Zurich (CH)

( * ) Notice: Subject to any disclaimer, the term of this patent is extended or adjusted under 35 U.S.C. 154(b) by 129 days.

(21) Appl. No.: 14/102,533

(22) Filed: Dec. 11, 2013

(65) Prior Publication Data
US 2014/0100278 A1 Apr. 10, 2014

Related U.S. Application Data

(62) Division of application No. 13/387,838, filed as application No. PCT/EP2010/004582 on Jul. 27, 2010, now abandoned.

(30) Foreign Application Priority Data

Jul. 30, 2009 (EP) .................................... 09009873

(51) Int. Cl.
| | |
|---|---|
| *C07C 59/115* | (2006.01) |
| *A61K 31/00* | (2006.01) |
| *A61K 31/045* | (2006.01) |
| *A61K 31/16* | (2006.01) |
| *A61K 31/185* | (2006.01) |
| *A61K 31/197* | (2006.01) |
| *A61K 31/198* | (2006.01) |
| *A61K 31/22* | (2006.01) |
| *A61K 31/341* | (2006.01) |
| *C07C 31/38* | (2006.01) |
| *C07C 229/20* | (2006.01) |

(52) U.S. Cl.
CPC ............... *C07C 59/115* (2013.01); *A61K 31/00* (2013.01); *A61K 31/045* (2013.01); *A61K 31/16* (2013.01); *A61K 31/185* (2013.01); *A61K 31/197* (2013.01); *A61K 31/198* (2013.01); *A61K 31/22* (2013.01); *A61K 31/341* (2013.01); *C07C 31/38* (2013.01); *C07C 229/20* (2013.01)

(58) Field of Classification Search
CPC ...................................................... A61K 31/16
See application file for complete search history.

(56) References Cited

U.S. PATENT DOCUMENTS

| | | | |
|---|---|---|---|
| 5,874,469 | A | 2/1999 | Maniar et al. |
| 7,947,727 | B2 | 5/2011 | Biggadike et al. |
| 2007/0207995 | A1 | 9/2007 | Salituro et al. |
| 2007/0276041 | A1 | 11/2007 | Oonuki et al. |
| 2008/0103139 | A1 | 5/2008 | Ishizuka et al. |
| 2009/0170917 | A1 | 7/2009 | Lee et al. |
| 2010/0004266 | A1 | 1/2010 | Masuda |
| 2010/0123883 | A1 | 5/2010 | Ohmura |

FOREIGN PATENT DOCUMENTS

| | | |
|---|---|---|
| EP | 1076563 | 2/2001 |
| EP | 1806342 | 7/2007 |
| EP | 2048138 | 4/2009 |
| WO | WO 99/53965 A1 | 10/1999 |
| WO | WO 02/03958 A1 | 1/2002 |
| WO | WO 02/066028 A2 | 8/2002 |
| WO | WO 2004/032858 | 4/2004 |
| WO | WO 2005/063690 A1 | 7/2005 |
| WO | WO 2005/097084 | 10/2005 |
| WO | WO 2007/041130 | 4/2007 |
| WO | WO 2007/142158 A1 | 12/2007 |
| WO | WO 2008/043789 | 4/2008 |
| WO | WO 2009/073665 | 6/2009 |

OTHER PUBLICATIONS

Cho et al., "The Effects of Sevoflurane on Systemic and Pulmonary Inflammatory Responses After Cardiopulmonary Bypass," *Journal of Cardiothoracic and Vascular Anesthesia*, vol. 23 No. 2, 639-645, 2009.
Han J. et al., "Trifluoroacetic Acid Activates ATP-Sensitive K+ Channels in Rabbit Ventricular Myocytes," *Biochemical and Biophysical Research Communications* vol. 285 No. 5.,1136-1142, 2001.
Steurer M. et al., "The Volatile Anaesthetic Sevoflurane Attenuates Lipopolysaccharide-Induced Injury in Alveolar Macrophages," *The Journal of Translational Immunology*, 155:224-230, 2009.
Kim et al., "2,2,2-Trifluoroethanol Toxicity in Aged Rats," *Toxicol. Pathol.* vol. 16 No. 1 35-45, 1988.
Mouw et al., "Caspase-9 Inhibition After Focal Cerebral Ischemia Improves Outcome Following Reversible Focal Ischemia," *Metab Brain Dis*, SEP (3), 143-151, 2002 <Abstract Only>.
Doillon et al., "Chemical Inactivators as Sterilization Agents for Bovine Collagen Materials," *J. Biomed Mat Res*, 37:212-221, 1997 <Abstract Only>.

*Primary Examiner* — Jake Vu
(74) *Attorney, Agent, or Firm* — JMB Davis Ben-David (57) ABSTRACT

The present invention relates to compounds according to formula (I) for medical use. The compounds are particularly suitable for the treatment and/or prevention of a medical condition involving hypoxic, anoxic and/or inflamed mammalian tissue. Furthermore, the invention relates to the use of said compounds for preparing a medicament and to pharmaceutical preparations comprising such compounds. The invention also relates to methods of treating or protecting patients having or being prone to develop a medical condition involving hypoxic, anoxic and/or inflamed mammalian tissue, the methods comprising administration of a therapeutically effective amount of such compounds.

7 Claims, 2 Drawing Sheets

INJECTABLE FORMULATION FOR TREATMENT AND PROTECTION OF PATIENTS HAVING AN INFLAMMATORY REACTION OR AN ISCHEMIA-REPERFUSION EVENT

CROSS REFERENCE TO RELATED APPLICATIONS

This is a divisional of co-pending U.S. patent application Ser. No. 13/387,838, which is the U.S. National Stage of International Application No. PCT/EP2010/004582, filed Jul. 27, 2010, which was published in English under PCT Article 21(2), which in turn claimed the benefit of European Patent Application No. 09009873.2, filed Jul. 30, 2009.

FIELD OF THE INVENTION

The present invention relates to compounds according to formula (I) for medical use. The compounds are particularly suitable for the treatment and/or prevention of a medical condition involving hypoxic, anoxic and/or inflamed mammalian tissue. Furthermore, the invention relates to the use of said compounds for preparing a medicament and to pharmaceutical preparations comprising such compounds. The invention also relates to methods of treating or protecting patients having or being prone to develop a medical condition involving hypoxic, anoxic and/or inflamed mammalian tissue, the methods comprising administration of a therapeutically effective amount of such compounds.

BACKGROUND OF THE INVENTION

Inflammatory reactions and ischemia-reperfusion processes belong to the most frequently occurring disease states in critically ill patients. Inflammatory syndromes such as severe inflammatory response syndrome, sepsis, acute lung injury and its progression to the acute respiratory distress syndrome (ARDS) remain leading factors of hospital morbidity and mortality. Damage to tissue as a result of an ischemia-reperfusion situation is especially frequent in myocardial, vascular and neuronal/cerebral tissue. Other tissues that are susceptible to an ischemia-reperfusion injury include tissues from liver, gut, kidney and eye.

The tissue's response to an injury or an infection results in an inflammatory reaction regulated by the coordinated function of cytokines, chemokines, adhesion molecules and tissue damage markers. Monocyte chemotactic protein-1 (MCP-1) and cytokine-induced neutrophil chemoattractant 1 (CINC-1) play crucial roles in the inflammatory orchestration upon injury and infection. The release of proinflammatory mediators like CINC-1, MCP-1 and other immunomodulating chemokines or cytokines results in recruitment of effector cells (such as neutrophiles and monocytes). These effector cells have an important role in the further development of injury.

It has been shown that volatile anesthetics like Isoflurane, Sevoflurane, Desflurane, Halothane and Enflurane have a positive influence on organs damaged by an inflammatory process or an ischemic event (Yue et al., Eur. Respir. J. 2008; 31(1): 118-125; Suter et al., Anesth. Analg. 2007; 104(3): 638-45). Administration of said volatile anesthetics (e.g. Sevoflurane, Isoflurane or Desflurane) significantly reduces inflammatory mediators and tissue damage markers (i.e. troponin or serum transaminase levels) in patients undergoing lung (De Conno et al., Anesthesiology 2009; 110:1316-1326), heart (Landoni et al., Curr. Vasc. Pharmacol. 2008; 6:108-111) or liver surgery (Beck-Schimmer et al., Ann. Surg. 2008; 248:909-918). Several disadvantages are associated with the use of volatile anaesthetics for organ protection. Due to the anaesthetic side-effect patients have to be monitored and ventilated during administration in a controlled environment such as an operating room or an intensive care unit. Dosing especially in sub-anaesthetic concentrations is very difficult. Several attempts have been made to provide the protective effect of these drugs to a wider patient population. Believing that these effects are limited to volatile anaesthetics the current most advanced design tries to treat patients by administering formulations containing volatile anaesthetics (Lucchinetti et al., Anesth. Analg. 2008 May; 106(5):1346-9; Rao et al., Anesth. Analg. 2008 May; 106(5):1353-9; Musser et al., Anesth. Analg. 1999; 88: 671-5).

Such methods of treatment are for example described in US patent application 2004/0127578 A1, which is directed to the parenteral administration of a formulation containing a halogenated volatile anesthetic to a patient to improve the tissue's resistance to an ischemic event.

WO 03/013539 A1 relates to the use of 1-[2-(4-3-trifluoromethyl-phenyl)piperazin-1-yl)ethyl]-2,3-dihydro-1H-benzimidazol-2-one (Flibanserin) for producing a drug with a neuroprotective action. WO 03/013539 speculates on the use of said compound for the treatment or prevention of neurodegenerative diseases.

Volatile anaesthetics are hydrophobic and marginally soluble in water or other biological fluids such as blood. Therefore, their intravenous administration is only feasible by addition of emulsifiers and stabilization agents. These attempts fail in a clinical setting due to a lot of difficulties such as the anaesthetic side-effect of the anaesthetics, dosing problems or pain during injection caused by the emulsifier.

Summarizing the above, it is the object underlying the present invention to provide compounds for the prevention and/or treatment of damages due to hypoxic or anoxic conditions or inflammation in tissue of patients that exhibit no or reduced anaesthetic side-effects and that can be administered without the addition of emulsifiers and that preferably have a significant solubility in water.

DESCRIPTION OF THE INVENTION

Surprisingly, it was discovered that the tissue-protective effect is not restricted to volatile anaesthetics but is rather the result of the presence of a functional —$C(R^3)_2F$ group in a chemical compound, wherein each $R^3$ denotes independently of one another in each instance a substituent selected from the group consisting of H, F, Cl, Br, I and $C_1$ to $C_6$ alkyl. Preferably the functional —$C(R^3)_2F$ group is —$CH_2F$, —$CHF_2$ or —$CF_3$.

This finding enables the preparation of non-anaesthetic and water-soluble compounds as organ protective formulations. As volatile anaesthetics are hydrophobic and marginally soluble in water, the present invention overcomes the above mentioned problems by administering hydrophilic molecules comprising at least one functional —$C(R^3)_2F$ group.

By doing so, the inventors overcome dosing and solubility problems of present attempts using volatile anaesthetics because the inventive compounds easily can be mixed with water, blood or biological fluids and do not cause an injection pain. Furthermore, the formulation can be administered without continuous medical surveillance and is therefore less expensive and applicable for a wider patient population.

The present invention provides chemical compounds with one or multiple —$C(R^3)_2F$ functional groups for the treatment and protection of patients which are suffering from an ischemia-reperfusion event or from an inflammatory reaction. The chemical compound is preferably low in molecular weight and includes one or several polar functional groups ($R^1$) that increase solubility in water. Accordingly, in a preferred embodiment, the $C(R^3)_2F$-containing molecule is water-soluble and therefore easily distributed through the blood circulation. Another advantage of the water-solubility of the compounds of the invention is that the compounds can preferably be formulated without the addition of emulsifiers.

Accordingly, in a first aspect the above objects are solved by compounds of formula (I) for medical use:

$(R^1)_n$—$R^2$—$(C(R^3)_2F)_m$      (I), wherein
- n is 1 to 5, preferably 1 to 4, more preferably 1 to 3, even more preferably 1 or 2, and most preferably 1,
- m is 1 to 5, preferably 1 to 4, more preferably 1 to 3, even more preferably 1 or 2, and most preferably 1,
- $R^1$ denotes in each instance a polar functional group bound to $R^2$,
- $R^2$ denotes a linear or branched, substituted or non-substituted alkyl, alkenyl, alkynyl, alkylidene, aryl, heteroaryl or carbocycle, —$C(R^3)_2F$) denotes a group that is in each instance bound to $R^2$, and
- $R^3$ denotes independently of one another in each instance a substituent selected from the group consisting of H, F, Cl, Br, I, and $C_1$ to $C_6$ alkyl (e.g. $C_1$, $C_2$, $C_3$, $C_4$, $C_5$, or $C_6$ alkyl), as well as their diastereomers or enantiomers in the form of their acids, bases or salts of physiologically acceptable acids or bases.

Thus, compounds of the invention contain 1 to 5 (e.g. 1, 2, 3, 4 or 5) polar functional groups $R^1$ that are bound to $R^2$. Further, compounds of the invention contain 1 to 5 (e.g. 1, 2, 3, 4 or 5) functional —$(C(R^3)_2F)$ groups that are bound to $R^2$.

Preferably, $R^3$ in $C(R^3)_2F$ is independently of $R^3$ in any other $C(R^3)_2F$ group and independently of $R^3$ in the same $C(R^3)_2F$ group F or H, preferably in both instances F. Thus, preferred compounds of the invention contain 1 to 5 (e.g. 1, 2, 3, 4 or 5) functional groups that are independently from one another selected from —$CH_2F$, —$CHF_2$, or —$CF_3$.

Preferably, $R^2$ is a linear or branched, substituted or non-substituted $C_{1-15}$ alkyl, alkenyl, or cycloalkyl, preferably a $C_{1-10}$ alkyl, alkenyl or cycloalkyl, more preferably a $C_{1-6}$ alkyl, alkenyl or cycloalkyl, most preferably a $C_{1-4}$ alkyl (e.g. methyl, ethyl, n-propyl, iso-propyl, n-butyl, sec-butyl, iso-butyl or tert-butyl). Without wishing to be bound by theory the inventors believe that selecting $R^2$ to have less than sixteen carbon atoms, preferably less than seven, more preferably less than five results in a low molecular weight compound that exhibits an increased dose/response efficacy.

In preferred embodiments, the compounds of the invention according to formula (I) have less than 16 carbon atoms (i.e. between 1 and 15 carbon atoms), more preferably less than 11 carbon atoms (i.e. 1, 2, 3, 4, 5, 6, 7, 8, 9 or 10 carbon atoms), even more preferably less than 7 carbon atoms (i.e. 1, 2, 3, 4, 5 or 6 carbon atoms).

In preferred embodiments, $R^2$ is substituted, preferably substituted with 1 to 10 (e.g. 1, 2, 3, 4, 5, 6, 7, 8, 9 or 10), more preferably 1 to 6 substituents, most preferably 1 to 3 substituents, each substituent preferably being selected independently from one another from the group consisting of —F, —Cl, —Br, —I, —OH, —$NH_2$, —COOH, —$COOR^4$, —CHO, —C(O)—$R^4$, —$CONH_2$, and —$CONHR^4$; wherein $R^4$ is a linear or branched, substituted or unsubstituted $C_{1-10}$ alkyl, alkenyl or cycloalkyl.

In preferred embodiments, each $R^1$ is independently selected from the group consisting of —OH, —$NH_2$, —COOH, —$COOR^4$, —CHO, —C(O)—$R^4$, —$CONH_2$ and —$CONHR^4$; wherein $R^4$ is in each instance independently selected from linear or branched, substituted or non-substituted $C_{1-10}$ alkyl, alkenyl or cycloalkyl. In more preferred embodiments, each $R^1$ is independently selected from the group consisting of —OH, —$NH_2$, —COOH, and —$COOR^4$. In particularly preferred embodiments, each $R^1$ is —OH.

In preferred embodiments, the compounds of the invention are alcohols, amines, carboxylic acids or esters. In particularly preferred embodiments the compounds of the invention are selected from the group consisting of the following substances: 1,1,1,3,3,3-Hexafluoro-2-methyl-2-propanol (C4H4F6O), 2,2,3,4,4,4-Hexafluoro-1-butanol (C4H4F6O), Perfluoro-tert-butyl alcohol (C4HF9O); 2,2,3,3,3-Pentafluoro-1-propanol (C3H3F5O), 1,1,1,3,3,4,4,4-Octafluoro-2-butanol (C4H2F8O), 2,2,3,3,4,4,4-Heptafluoro-1-butanol (C4H3F7O), 1,1,1,3,3,3-Hexafluoropropan-2-ol (C3H2F6O), 2,2,2-Trifluoroethanol (C2H3F3O), 2-Hydroxy-2-(trifluoromethyl)propionitrile (C4H4F3NO), 3,4,4,4-Tetrafluoro-3-(trifluoromethyl)butan-1-ol (C5H5F7O), 2-(2,2,3,4,4,4-Hexafluorobutoxy)ethanol (C6H8F6O2), 2,2,2-Trifluoro-1-(furan-3-yl)ethanol (C6H5F3O2), N-Methyl-2,2,2-trifluoroacetamide (C3H4F3NO), 2,2,2-Trifluoroacetamide (C2H2F3NO), 3-Amino-4,4,4-trifluorobutyric acid (C4H6F3NO2), 3,3,3-Trifluoro-2-(hydroxymethyl)propanoic acid (C4H5F3O3), 4,4,4-Trifluoroacetoacetic acid methyl ester (C5H5F3O3), 5,5,5-Trifluorleucine.

The present invention also relates to compounds according to formula (I) that are volatile provided that such compounds are soluble in water. Such volatile, water-soluble compounds can be administered to the patient by injection (e.g. intravenously or intramuscularly) and are removed from the patient through the lungs.

Preferably, the compounds of the invention are soluble in water. One measure for the water solubility of a compound is its octanol-water partition coefficient. The octanol-water partition coefficient ($K_{ow}$) is defined as the ratio of a compound's concentration in the octanol phase to its concentration in the aqueous phase of a two-phase octanol/water system. Values of $K_{ow}$ are thus unitless. The parameter is typically measured using low solute concentrations, where $K_{ow}$ is a very weak function of solute concentration. Values of $K_{ow}$ are usually measured at room temperature (20 or 25° C.). Measured values of $K_{ow}$ for organic chemicals have been found as low as $10^{-3}$ and as high as $10^7$, thus encompassing a range of ten orders of magnitude. In terms of log $K_{ow}$, this range is from −3 to 7.

The chemical in question is added to a mixture of octanol and water whose volume ratio is adjusted according to the expected value of $K_{ow}$. Very pure octanol and water must be used, and the concentration of the chemical in the system should be less than 0.01 mol/L. The system is shaken gently until equilibrium is achieved (15 min to 1 hr). Centrifugation is generally required to separate the two phases, especially if an emulsion has formed. An appropriate analytical technique is then used to determine the solute concentration in each phase. A rapid laboratory estimate of $K_{ow}$ may be obtained by measuring the retention time in a high-pressure liquid chromatography system; the logarithm of the retention time and the logarithm of $K_{ow}$ have been found to be linearly related.

Chemicals with low $K_{ow}$ values (e.g., less than 10) may be considered relatively hydrophilic; they tend to have high water solubilities. Conversely, chemicals with high $K_{ow}$ values (e.g., greater than $10^4$) are very hydrophobic.

Preferably, the compounds of the invention have an octanol-water partition coefficient of less than 20, more preferably less than 15, more preferably less than 10, more preferably less than 5, more preferably less than 1. In particularly preferred embodiments, the compounds of the invention are completely miscible with water.

Preferred compounds of the invention do not have anaesthetic side-effects at suitable concentrations for the inventive indications.

In a preferred embodiment of the first aspect, the compound is not 1-[2-(4-3-trifluoromethyl-phenyl)piperazin-1-yl)ethyl]-2,3-dihydro-1H-benzimidazol-2-one (Flibanserin) nor a salt thereof.

In a further aspect, the above objects are solved by compounds of the invention as defined above for the treatment and/or prevention of a medical condition involving hypoxic, anoxic and/or inflamed mammalian tissue. Preferably, the tissue is selected from the group consisting of heart, lung, liver, brain, gut, kidney, muscle, bone, skin and eye.

The compounds of the invention are suitable for administration prior to, after or concomitantly to a medical condition involving hypoxic, anoxic and/or inflamed mammalian tissue, preferably ischemia reperfusion injury, inflammation or a medical intervention, preferably surgery or catheterization.

DEFINITIONS

In the context of the present invention it is understood that antecedent terms such as "linear" or "branched", "substituted" or "non-substituted" indicate that each one of the subsequent terms is to be interpreted as being modified by said antecedent term. For example, the scope of the term "linear or branched, substituted or non-substituted alkyl, alkenyl, alkynyl, alkylidene, carbocycle" encompasses linear or branched, substituted or non-substituted alkyl; linear or branched, substituted or non-substituted alkenyl; linear or branched, substituted or non-substituted alkynyl; linear or branched, substituted or non-substituted alkylidene; and linear or branched, substituted or non-substituted carbocycle. For example, the term "$C_2$-$C_{12}$ alkenyl, alkynyl or alkylidene" indicates the group of compounds having 2 to 12 carbons and alkenyl, alkynyl or alkylidene functionality.

In all compounds disclosed herein, in the event that the nomenclature conflicts with the structure, it shall be understood that the compound is defined by the structure.

The term "heteroatom", as used herein, shall be understood to mean atoms other than carbon and hydrogen such as and preferably O, N, S and P.

The terms alkyl, alkenyl, alkynyl, alkylidene, etc. shall be understood as encompassing linear as well as branched forms of carbon-containing chains where structurally possible. In these carbon chains one or more carbon atoms can be optionally replaced by heteroatoms, preferably by O, S or N. If N is not substituted, it is NH. The heteroatoms may replace either terminal or internal carbon atoms within a linear or branched carbon chain. Such groups can be substituted as herein described by groups such as oxo to result in definitions such as but not limited to alkoxycarbonyl, acryl, amido and thioxo.

The term "carbocycle" shall be understood to mean an aliphatic hydrocarbon radical containing from 3 to 20, preferably 3 to 12 carbon atoms, more preferably 5 or 6 carbon atoms. Carbocycles include hydrocarbon rings containing from 3 to 20, preferably 3 to 10 carbon atoms. These carbocycles may be either aromatic or non-aromatic systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl, and benzocycloheptenyl. Certain terms for cycloalkyl such as cyclobutanyl and cyclobutyl shall be used interchangeably.

The term "cycloalkyl" shall be understood to mean aliphatic hydrocarbon-containing rings having from 3 to 20, preferably 3 to 12 carbon atoms. These non-aromatic ring systems may be mono- or polyunsaturated, i.e. the term encompasses cycloalkenyl and cycloalkynyl. The cycloalkyl may comprise heteroatoms, preferably O, S or N, and be substituted or non-substituted. Preferred and non-limiting cycloalkyls include cyclopropyl, cyclobutyl, cyclopentyl, cyclopentenyl, cyclohexyl, cyclohexenyl, cycloheptanyl, cycloheptenyl, benzocyclobutanyl, benzocycloheptanyl and benzocycloheptenyl.

The term "heterocyclic" refers to a stable non-aromatic, preferably 3 to 20-membered, more preferably 3 to 12-membered, most preferably 5 or 6-membered, monocyclic or multicyclic, preferably 8 to 12-membered bicyclic, heteroatom-containing cyclic radical, that may be either saturated or unsaturated. Each heterocycle consists of carbon atoms and one or more, preferably 1 to 4 heteroatoms chosen from nitrogen, oxygen and sulphur. The heterocyclic residue may be bound to the remaining structure of the complete molecule by any atom of the cycle, which results in a stable structure. Exemplary heterocycles include, but are not limited to, pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-aza-tricyclo[7.3.1.0-2,7]tridecy-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulphide, pentamethylene sulfoxide, pentamethylene sulfone, tetramethylene sulphide, tetramethylene sulfoxide and tetramethylene sulfone.

The term "aryl" as used herein shall be understood to mean an aromatic carbocycle or heteroaryl as defined herein. Each aryl or heteroaryl unless otherwise specified includes its partially or fully hydrogenated derivative. For example, quinolinyl may include decahydroquinolinyl and tetrahydroquinolinyl; naphthyl may include its hydrogenated derivatives such as tetrahydronaphthyl. Other partially or fully hydrogenated derivatives of the aryl and heteroaryl compounds described herein will be apparent to one of ordinary skill in the art. Naturally, the term encompasses aralkyl and alkylaryl, both of which are preferred embodiments for practicing the compounds of the present invention. For example, the term aryl encompasses phenyl, indanyl, indenyl, dihydronaphthyl, tetrahydronaphthyl, naphthyl and decahydronaphthyl.

The term "heteroaryl" shall be understood to mean an aromatic $C_3$-$C_{20}$, preferably 5 to 8-membered monoxyclic or preferably 8 to 12-membered bicyclic ring containing 1 to 4 heteroatoms such as N, O and S. Exemplary heteroaryls comprise aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazole[3,4-b]pyridinyl, tubercidinyl, oxazo[4,5-b]pyridinyl and imidazo[4,5-b]pyridinyl.

Terms which are analogues of the above cyclic moieties such as aryloxy or heteroaryl amine shall be understood to mean an aryl, heteroaryl, heterocycle as defined above attached to its respective group.

As used herein, the terms "nitrogen" and "sulphur" include any oxidized form of nitrogen and sulphur and the quaternized form of any basic nitrogen as long as the resulting compound is chemically stable. For example, for an —S—$C_{1-6}$ alkyl radical shall be understood to include —S(O)—$C_{1-6}$ alkyl and —S(O)$_2$—$C_{1-6}$ alkyl.

The compounds of the invention are only those which are contemplated to be 'chemically stable' as will be appreciated by those skilled in the art. For example, compounds having a 'dangling valency' or a 'carbanion' are not compounds contemplated by the inventive concept disclosed herein.

Methods of Preparation

The compounds and precursor compounds of the present invention can be prepared without any undue burden or inventive skill by any appropriate conventional synthetic strategy known to those of skill in organic chemistry. Some of the compounds of the present invention or direct precursors thereof may also be commercially available.

Medical Use and Pharmaceutical Compositions

The invention includes pharmaceutically acceptable derivatives of compounds of formula (I). A "pharmaceutically acceptable derivative" refers to any pharmaceutically acceptable salt or ester or any other compound which, upon administration to a patient, is capable of providing (directly or indirectly) a compound of the invention or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium, potassium), alkaline earth metal (e.g. magnesium), ammonium and N—($C_1$-$C_4$ alkyl)$_4^+$ salts.

In addition, the scope of the invention also encompasses prodrugs of compounds of formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

In view of the above and because the compounds of the invention have demonstrated immunomodulatory effects on epithelial and endothelial cells, another aspect of the present invention relates to pharmaceutical compositions comprising at least one compound of the invention as defined above or pharmaceutically acceptable derivatives or prodrugs thereof, and optionally one or more physiologically acceptable excipients and/or carriers.

In a further aspect, the present invention relates to a use of a compound of the invention as defined above for the preparation of a medicament for the treatment and/or protection of patients having or being prone to produce a medical condition involving hypoxic, anoxic and/or inflamed mammalian tissue, preferably a tissue selected from the group consisting of heart, lung, liver, brain, gut, kidney, muscle, bone, skin and eye, preferably a medical condition selected from ischemia reperfusion injury, severe inflammatory response syndrome, sepsis, organ transplantation, organ resection, organ or implant rejection, inflammation, e.g. due to allergy or infection, e.g. asthma, psoriasis, pneumonia, etc., or related to a medical intervention, preferably surgery or catheterization. The pharmaceutical composition is for administration prior to, after or concomitantly to a medical condition.

The compounds of the present invention are particularly useful for preparing a medicament for inhalative treatment. In a preferred embodiment, the compounds of the present invention are formulated as a pharmaceutical composition for inhalative administration for the prophylaxis and/or treatment of inflammatory diseases, preferably inflammatory diseases of the respiratory system such as e.g. asthma, pneumonia, or cardiac conditions such as cardiac infarction.

In a preferred alternative, the compounds of the present invention can be formulated for topical administration, preferably as dressing, ointment, lotion, plaster, spray, etc. This type of administration is particularly useful for treating a skin inflammation, e.g. resulting from a skin wound, skin infection or allergy.

As used herein, a "patient" means any mammal that may benefit from a treatment with the compounds according to formula (I) described herein. Preferably, a "patient" is selected from the group consisting of laboratory animals (e.g. mouse or rat), domestic animals (including e.g. guinea pig, rabbit, pig, sheep, goat, camel, cow, horse, donkey, cat, or dog), or primates including human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "administering" includes in vivo administration, as well as administration directly to tissue ex vivo, such as vein grafts. Administration may be effected for the prevention, i.e. before clinical occurrence of a disease or disorder, or for treatment, i.e. after clinical occurrence of a disease or disorder.

Methods of Use

In a further aspect, the present invention relates to a method of treating and/or protecting patients having or being prone to develop a medical condition involving hypoxic, anoxic and/or inflamed mammalian tissue, preferably a tissue selected from the group consisting of heart, lung, liver, brain, gut, kidney, muscle, bone, skin and eye, preferably a medical condition selected from ischemia reperfusion injury, inflammation or related to a medical intervention, preferably surgery or catheterization, the method comprising the administration of a therapeutically effective amount of a compound of the invention as defined above or a prodrug thereof or an effective amount of the pharmaceutical composition of the invention as defined above to a patient in need thereof.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

For therapeutic or prophylactic use the compounds of the invention may be administered in any conventional dosage form in any conventional manner. Routes of administration include, but are not limited to, intravenously, intramuscularly, subcutaneously, intrasynovially, by infusion, sublingually, transdermally, orally, inhalative or topically. The preferred modes of administration are intravenous, intrathecal, intraperitoneal, peri- or epidural, subcutaneous, intramuscular or topical.

The compounds may be administered alone or in combination with adjuvants that enhance stability of the compounds, facilitate administration of pharmaceutical compositions containing them in certain embodiments, provide increased dissolution or dispersion, provide adjunct therapy, and the like, including other active ingredients. Advantageously such combination therapies utilize lower dosages of the conventional therapeutics, thus avoiding possible toxicity and adverse side-effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminium stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Controlled release dosage forms with or without immediate release portions are also envisaged. Methods for preparing such dosage forms are known (see, for example, H. C. Ansel and N. G. Popovish, Pharmaceutical *Dosage Forms and Drug Delivery Systems*, 5$^{th}$ ed., Lea and Febiger (1990)). Dosage levels and requirements are well-recognized in the art and may be selected by those of ordinary skill in the art from available methods and techniques suitable for a particular patient. In some embodiments, dosage levels range from about 0.1-100 g/dose for a 70 kg patient. Although one dose per day may be sufficient, up to 5 doses per day may be given. For oral doses, up to 2000 mg/day or more may be required.

Reference in this regard may also be made to U.S. provisional application No. 60/339,249. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician.

As noted above, some embodiments of the present invention refer to hydrophilic non-volatile compounds according to formula (I). Such non-volatile substances can be applied intravenously for organ protection. This procedure can be used in situations of any hypoxic or inflammatory organ injury and independent of the localization of the patient (intensive care unit, emergency room, perioperative care, etc). In an exemplary embodiment, a patient experiences an occlusion of one of the inflow vessels to the heart (ischemia). This leads to hypoxic conditions in the heart's tissue. In the coronary angiography, where the clot in the vessel is detected and should be removed, followed by reperfusion of the heart (reperfusion damage), the patient receives a pharmaceutical compound of the invention as described above before, during and/or after the intervention.

As noted above, some embodiments of the present invention refer to hydrophilic volatile compounds according to formula (I). Such volatile pharmaceutical compounds can be given intravenously, but will be eliminated as volatile substances through the lungs. This implies a short time of metabolic transformation in the body of the patient and allows an on-site adjustment of intravenously applied doses e.g. by measuring the exhaled concentration of the volatile compound described above. In exemplary embodiment, a patient suffers from a sepsis (serious medical condition characterized by a whole-body inflammatory state, including several organs such as kidneys, liver, lungs or heart). A volatile pharmaceutical compound of the invention is given to the patient over a longer period of time to protect the organ, most common in the operating theatre or the intensive care unit. By measuring the concentration of the compound in the exhaled air of the patient dosing can be controlled and optimized. The elimination of the compound through the lungs is especially an advantage in patients suffering from a decreased metabolization capacity as liver or renal function is deteriorated in such states of critical illness.

In a further aspect, the present invention pertains to a medical device for temporary or permanent introduction into a mammalian body, preferably an implant or transplant organ, comprising at least one surface coated with at least one of the compounds of the invention, preferably selected from the group consisting of bone, tooth and cartilage implants, syringes, catheters, electrodes, stents and cardiac pacemakers. The medical device may be partially or fully introduced into the mammalian body. The medical devices of the present invention have the advantage that their inventive compound coating reduces or inhibits inflammatory reactions resulting from their introduction into the mammalian body. In another embodiment the coating is provided as a controlled release coating that allows for the coated compounds to diffuse into the adjacent tissues in a time-controlled manner.

The following tables, figures and examples are merely illustrative of the present invention and should not be construed to limit the scope of the invention as indicated by the appended claims in any way.

SHORT DESCRIPTION OF THE FIGURES/TABLES

Table 1 CINC-1/GROa protein levels of human blood micro vascular endothelial cells measured in supernatants in relation to an exposition to LPS without any substance (positive control=100%)

Table 2 MCP-1 levels of rat alveolar epithelial cells measured in supernatants in relation to an exposition to LPS without any substance (positive control=100%)

Table 3 Comparison of compound properties

EXAMPLES

Example 1

Protective Effects of Molecules Containing CF3-Groups on Epithelial and Endothelial Cells INTRODUCTION: Inflammatory reactions and ischemia-reperfusion processes belong to the most frequently occurring disease states in critically ill patients (Phua et al.: Has mortality from acute respiratory distress syndrome decreased over time?: A systematic review. Am. J. Respir. Crit. Care Med 2009; 179: 220-7). It has been shown that lipopolysaccharide (LPS)-induced injury is a very useful experimental model for the investigation and characterization of immunopathogenic changes and mechanisms of a tissue injury. The response to LPS results in an inflammatory reaction regulated by the coordinated function of cytokines, chemokines, and adhesion molecules. Monocyte chemotactic protein-1 (MCP-1) and cytokine-induced neutrophil chemoattractant 1 (CINC-1) play crucial roles in the inflammatory orchestration upon injury and infection (Ulich et al., Am. J. Physiol. 1995; 268:L245-50; van Helden et al., Exp. Lung Res. 1997; 23:297-316; Beck-Schimmer et al., Respir. Res. 2005 Jun. 22; 6:61; Zagorski et al., J. Immunol. 2007 Dec. 1; 179(11):7820-6).

METHODS: Different molecules with CF3-group were tested against their corresponding non-fluorinated molecules. The group of molecules with CF3-group included hexafluoroisopropanol, 2,2,3,3,3-pentafluoro-1-propanol, 2,2,2-trifluorethanol, 3-amino-4,4,4-trifluorobutyroic acid, methyl-4,4,4-trifluoro-acetoacetate, methyl-trifluoro-acetamide, 5,5,5-trifluorleucine and Sevoflurane. In the group without CFx moieties 2-propanol, 1-propanol, ethanol, leucine, and diethyl ether were included. As well established model rat alveolar epithelial cells (AEC) and human blood microvascular cells (HMVEC) were exposed to phosphate-buffered saline (PBS, negative control) or LPS (20 μg/ml) for 6 hours (positive control). The influence of fluorinated compounds and non-fluorinated reference compounds on the inflammatory response of the cells was tested. Expression of rat-MCP-1 (BD Biosciences, San Diego, Calif.) and human CINC-1 GROa (R&D Systems Europe Ltd.) protein were analyzed by ELISA.

Evaluation of possible cytotoxicity was done counting cells by means of fluorescence DNA quantification assays. At the same time release of lactate dehydrogenase into the supernatants was measured (LDH Assay, Promega, Madison, Wis., USA).

Furthermore, the effect of hexafluoro-2-propanol in a concentration of 16 mmol/L on the chemotactic migration of polymorphonuclear neutrophils towards supernatants from LPS-stimulated endothelial cells (right side, 270°) and towards supernatants from LPS-stimulated endothelial cells incubated with hexafluoro-2-propanol (left side, 90°) was assessed according to (De Conno et al., Anesthesiology 2009; 110:1316-1326)

Figure 1:
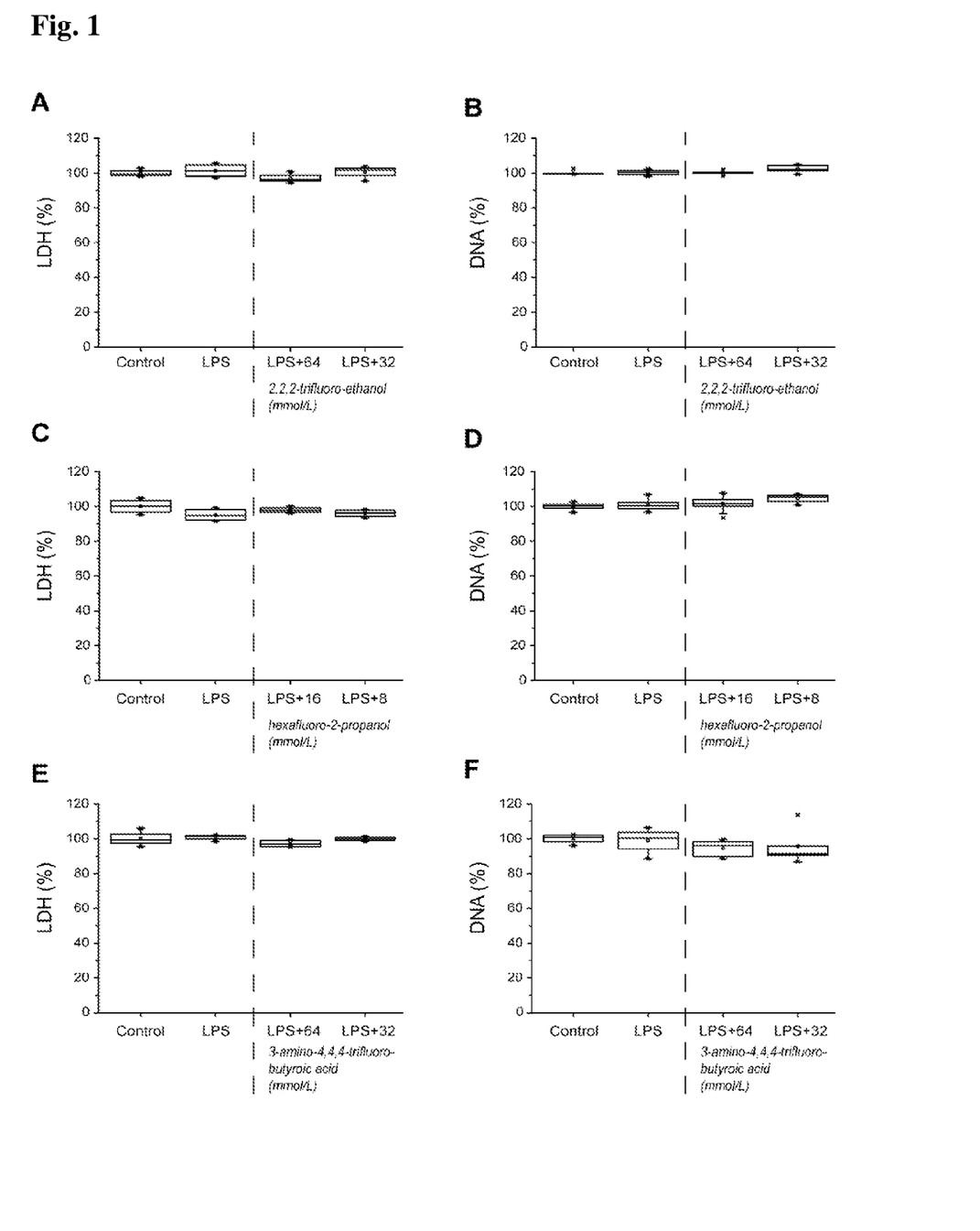
FIG. 1 shows the effects on viability and cytotoxicity in human microvascular endothelial cells (HMVEC) after administration of 2,2,2-trifluoro-ethanol (A, B), hexafluoro-2-propanol (C, D) and 3-amino-4,4,4-trifluorobutyroic acid (E, F). Viability is assessed by measuring the release of lactate dehydrogenase and cytotoxicity is quantified by counting cells by means of fluorescence DNA quantification assays (see example 1). The administration of CF3-containing compounds does not cause significant cytotoxicity. Hence, these compounds are suitable for in vivo administration to mammals in need thereof. Concentration level differences are presented in relation to control (100%).
Figure 2:
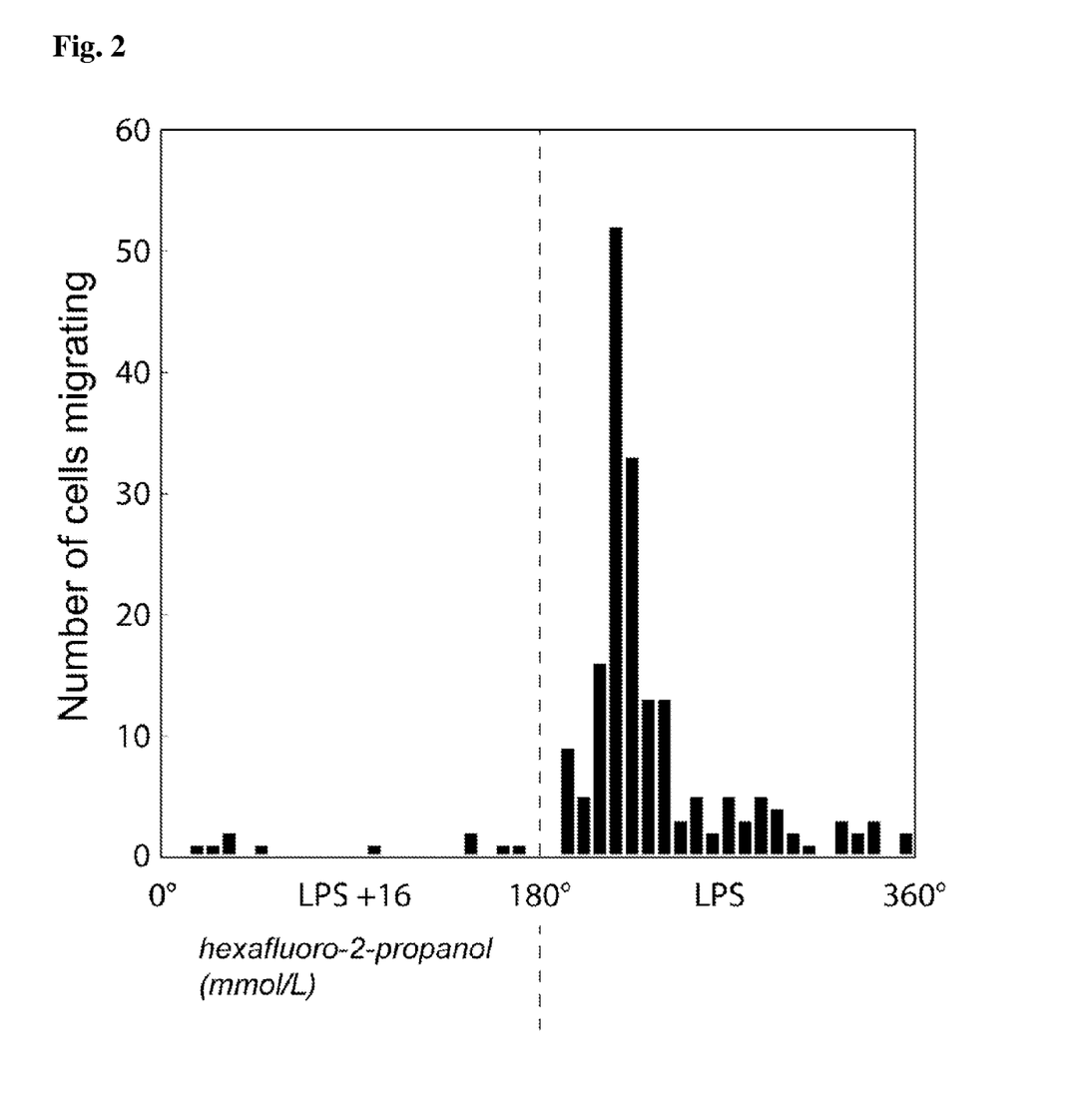
FIG. 2 shows a graph representing the results of administration of 16 mmol/L hexafluoride-2-propanol to polymorphonuclear neutrophils in chemotactic migration assays that demonstrates the combined effects of hexafluoro-2-propanol on inflammatory mediator secretion and effector cell recruitment.

RESULTS: MCP-1 and CINC-1 levels of endothelial and epithelial cells stimulated with LPS were in a dose-dependent manner significantly decreased by exposure to molecules with CF3-group(s). The decrease was most pronounced using hexafluoroisopropanol having two CF3-groups (CF3-group concentration dependency). This decrease of MCP-1 and CINC-1 levels upon LPS stimulation could not be shown for their non-fluorinated counterparts (same time course, same concentrations). The decrease of inflammatory mediators leads to a significantly attenuated chemotaxis for neutrophils (see FIG. 2).

CONCLUSIONS: The results show that molecules containing at least one CF3-Group have immunomodulatory effects on epithelial and endothelial cells. The effect has been shown for both animal and human cell lines. The biological relevance of the shown immunomodulatory effects was confirmed by performing chemotactic migration assays, thus demonstrating that an attenuation of the expression of inflammatory mediators represents not only a quantitative phenomenon, but evokes also qualitative consequences: with less neutrophils the tissue damage will be decreased. A hydrophilic pharmaceutical formulation containing molecules having at least one CF3-group is therefore beneficial for treating patients suffering from an inflammatory process or an ischemia-reperfusion injury.

TABLE 1

HMVEC results

| Substance | | Concentration in culture medium | | $25^{th}$ percentile | Median | 75th percentile |
|---|---|---|---|---|---|---|
| with CFx-group | | | | | | |
| 2,2,2-Trifluor-ethanol | $C_2H_3F_3O$ | 64 | mmol/l | 69 | 73 | 76 |
| | | 32 | mmol/l | 76 | 78 | 79 |
| | | 16 | mmol/l | 93 | 98 | 100 |
| 2,2,3,3,3-Pentafluoro-1-propanol | $C_3H_3F_5O$ | 64 | mmol/l | 30 | 31 | 31 |
| | | 32 | mmol/l | 40 | 41 | 42 |
| | | 16 | mmol/l | 106 | 115 | 128 |
| Hexafluoro-isopropanol | $C_3H_2F_6O$ | 16 | mmol/l | 22 | 26 | 28 |
| | | 4 | mmol/l | 46 | 49 | 51 |
| 3-Amino-4,4,4-Trifluoro-butyroic acid | $C_4H_6F_3NO_2$ | 64 | mmol/l | 0 | 0 | 0 |
| | | 16 | mmol/l | 0 | 0 | 1 |
| | | 8 | mmol/l | 75 | 79 | 80 |
| without CFx-group | | | | | | |
| Ethanol | $C_2H_6O$ | 64 | mmol/l | 85 | 88 | 95 |
| | | 32 | mmol/l | 88 | 91 | 92 |
| | | 16 | mmol/l | 104 | 107 | 115 |
| 1-Propanol | $C_3H_8O$ | 64 | mmol/l | 51 | 64 | 67 |
| | | 32 | mmol/l | 80 | 81 | 82 |
| | | 16 | mmol/l | 81 | 82 | 86 |
| 2-Propanol | $C_3H_8O$ | 16 | mmol/l | 91 | 97 | 97 |
| | | 4 | mmol/l | 107 | 109 | 110 |

TABLE 2 rat alveolar epithelial cells results

| Substance | | Concentration in culture medium | | 25th percentile | Median | 75th percentile |
|---|---|---|---|---|---|---|
| with CFx-group | | | | | | |
| 2,2,2-Trifluorethanol | $C_2H_3F_3O$ | 64 | mmol/l | 55 | 59 | 60 |
| | | 16 | mmol/l | 55 | 58 | 63 |
| Hexafluoroisopropanol | $C_3H_2F_6O$ | 32 | mmol/l | 0 | 11 | 16 |
| | | 16 | mmol/l | 53 | 63 | 74 |
| | | 8 | mmol/l | 96 | 101 | 107 |
| | | 4 | mmol/l | 97 | 98 | 101 |
| 2,2,3,3-Pentafluoro-1-propanol | $C_3H_3F_5O$ | 64 | mmol/l | 54 | 70 | 76 |
| | | 16 | mmol/l | 83 | 92 | 101 |
| 3-Amino-4,4,4-trifluorobutyroic acid | $C_4H_6F_3NO_2$ | 64 | mmol/l | 0 | 0 | 0 |
| | | 32 | mmol/l | 43 | 44 | 46 |
| | | 16 | mmol/l | 88 | 101 | 124 |
| Sevoflurane | $C_4H_3F_7O$ | 64 | mmol/l | 60 | 68 | 72 |
| Methyl-4,4,4-trifluoro-acetoacetate | $C_5H_5F_3O_3$ | 32 | mmol/l | 0 | 0 | 1 |
| | | 16 | mmol/l | 6 | 7 | 8 |
| Methyltrifluoroacetamide | $CF_3CONHCH_3$ | 64 | mmol/l | 0 | 0 | 0 |
| | | 32 | mmol/l | 32 | 41 | 48 |
| | | 16 | mmol/l | 53 | 56 | 81 |
| | | 8 | mmol/l | 68 | 80 | 81 |
| 5,5,5-Trifluorleucine | $C_6H_{10}F_3NO_2$ | 16 | mmol/l | 66 | 68 | 70 |
| without CFx-group | | | | | | |
| Ethanol | $C_2H_6O$ | 64 | mmol/l | 86 | 92 | 94 |
| | | 16 | mmol/l | 97 | 103 | 121 |
| 2-Propanol | $C_3H_8O$ | 64 | mmol/l | 78 | 82 | 87 |
| | | 32 | mmol/l | 82 | 86 | 92 |
| | | 16 | mmol/l | 98 | 101 | 110 |
| 1-Propanol | $C_3H_8O$ | 64 | mmol/l | 71 | 74 | 77 |
| | | 16 | mmol/l | 96 | 99 | 104 |
| DL-3-Amino-n-butyric acid | $C_4H_9NO_2$ | 64 | mmol/l | 112 | 117 | 130 |
| | | 32 | mmol/l | 127 | 149 | 171 |
| | | 16 | mmol/l | 90 | 91 | 100 |
| | | 8 | mmol/l | 93 | 95 | 97 |
| Chloroform | $C_1H_1Cl_3$ | 64 | mmol/l | 170 | 171 | 177 |
| Leucine | $(CH_3)_2CHCH_2CH-(NH_2)CO_2H$ | 16 | mmol/l | 90 | 91 | 91 |

TABLE 3 comparison of compound properties

| | | Boiling point | Melting point |
|---|---|---|---|
| 2,2,2-Trifluoroethanol | (structure) | 78.0° C. | |
| 1,1,1,3,3,3-Hexafluoropropan-2-ol | (structure) | 59° C. | |
| 2,2,3,3-Pentafluoro-1-propanol | (structure) | 81° C. | |
| 3-Amino-4,4,4-trifluorobutyric acid | (structure) | | 180-190° C. |

| | Blood:Gas Partition coefficient | Oil:Gas Partition coefficient | Octanol water Partition coefficient | Solubility |
|---|---|---|---|---|

TABLE 3-continued comparison of compound properties

| | | | |
|---|---|---|---|
| 2,2,2-Trifluoroethanol | (structure: CF3-CH2-OH) | 0.17 [1] | miscible |
| 1,1,1,3,3,3-Hexafluoropropan-2-ol | (structure: (CF3)2CH-OH) | 0.37 [1] | 1000/g/L (25° C.) |
| 2,2,3,3,3-Pentafluoro-1-propanol | (structure: CF3-CF2-CH2-OH) | | 21.9 g/L (25° C.) |
| 3-Amino-4,4,4-trifluorobutyric acid | (structure shown) | | |

| | | Boiling point | Melting point | Blood:Gas Partition Coefficient |
|---|---|---|---|---|
| Desflurane | (F3C-CHF-O-CHF2) | 22.8° C. | | 0.42 |
| Isoflurane | (structure) | 48.5° C. | | 1.4 |
| Enflurane | (structure) | 56.5° C. | | 1.9 |
| Sevoflurane | (structure) | 58.5° C. | | 0.68 |
| Halothane | (CF3-CHClBr) | 50.2° C. | | 2.5 |

| | | Oil:Gas Partition coefficient | Octanol water partition coefficient [2] | solubility |
|---|---|---|---|---|
| Desflurane | (structure) | 19 | 28.5 | |
| Isoflurane | (structure) | 98 | 156 | |

TABLE 3-continued comparison of compound properties

| Compound | Structure | | |
|---|---|---|---|
| Enflurane | F₃C-CH(CF₃)-O-CH₂F (structure) | 98 | 122 |
| Sevoflurane | (CF₃)₂CH-O-CHF₂ with Cl (structure shown) | 47 | 71 |
| Halothane | CF₃-CHClBr (structure) | 224 | 315 |

[1] Qiana et al., Journal of Chromatography A 1143, 1-2, 2007, 276-283.
[2] Urban et al., Anästhesiol. Intendicmed. Schmerzther. 1995;30;375-382

We claim:

1. A method for treating or inhibiting a condition selected from the group consisting of ischemia reperfusion injury, severe inflammatory response syndrome, sepsis, organ resection, and organ or implant rejection, the method comprising:
administering to a patient in need of such treatment or inhibition, a composition comprising:
a compound of formula (I):

$(R^1)_n—R^2—(CF_3)_m;$ wherein
n is 1 to 3,
m is 1 to 3,
$R^1$ is bound to $R^2$, and each $R^1$ is independently selected from the group consisting of —OH, —NH$_2$, and —COOH,
$R^2$ is:
a linear $C_{1-4}$ alkyl, substituted with 1 to 6 F substituents, —OH, —NH$_2$, and —COOH, or
a linear non-substituted $C_{1-4}$ alkyl, and
—(CF$_3$) is in each instance bound to $R^2$;
thereby treating or inhibiting the condition.

2. The method of claim 1, wherein R2 is substituted with 1 to 3 substituents.

3. The method of claim 1, wherein the compound of formula (I) is selected from the group consisting of:
1,1,1,3,3,3-Hexafluoro-2-methyl-2-propanol,
2,2,3,4,4,4-Hexafluoro-1-butanol,
Perfluoro-tert-butyl alcohol,
2,2,3,3,3-Pentafluoro-1-propanol,
1,1,1,3,3,4,4,4-Octafluoro-2-butanol,
2,2,3,3,4,4,4-Heptafluoro-1-butanol,
1,1,1,3,3,3-Hexafluoropropan-2-ol,
3,4,4,4-Tetrafluoro-3-(trifluoromethyl)butan-1-ol,
3-Amino-4,4,4-trifluorobutyric acid,
3,3,3-Trifluoro-2-(hydroxymethyl)propanoic acid, and
5,5,5-Trifluorleucine.

4. The method of claim 1, wherein the compound of formula (I) has an octanol-water partition coefficient of less than 20.

5. The method of claim 1, wherein the composition is a pharmaceutical composition formulated for inhalative administration.

6. The method of claim 5, wherein the administration is by inhalation.

7. The method of claim 1, wherein the administration is prior to, after or concomitant with the ischemia reperfusion injury, severe inflammatory response syndrome, sepsis, organ resection, organ or implant rejection, or condition arising from organ transplantation.

* * * * *